United States Patent
Aoki

(10) Patent No.: US 8,871,962 B2
(45) Date of Patent: Oct. 28, 2014

(54) METHOD FOR PRODUCING SANSHOOL

(75) Inventor: Katsuyuki Aoki, Ibaraki (JP)

(73) Assignee: Tsumura & Co., Tokyo (JP)

( * ) Notice: Subject to any disclaimer, the term of this patent is extended or adjusted under 35 U.S.C. 154(b) by 0 days.

(21) Appl. No.: 13/988,401

(22) PCT Filed: Nov. 28, 2011

(86) PCT No.: PCT/JP2011/077437
§ 371 (c)(1),
(2), (4) Date: May 20, 2013

(87) PCT Pub. No.: WO2012/073910
PCT Pub. Date: Jun. 7, 2012

(65) Prior Publication Data
US 2013/0245303 A1  Sep. 19, 2013

(30) Foreign Application Priority Data
Nov. 30, 2010  (JP) .................. 2010-267654

(51) Int. Cl.
C07F 15/02 (2006.01)
C07C 231/12 (2006.01)
C07C 233/12 (2006.01)

(52) U.S. Cl.
CPC ............... *C07C 231/12* (2013.01); *C07F 15/02* (2013.01)
USPC ......................................... 556/141; 564/204

(58) Field of Classification Search
USPC .......................................... 556/141; 564/204
See application file for complete search history.

(56) References Cited

U.S. PATENT DOCUMENTS

2013/0261327 A1* 10/2013 Aoki .............................. 556/141

FOREIGN PATENT DOCUMENTS

JP      1-294657 A    11/1989

OTHER PUBLICATIONS

Leslie Crombie et al., "Synthesis of Natural Polyene Isobutylamides. Stereochemistry of the Wittig Reactions", Tetrahedron Letters 1985, pp. 2481-2484, vol. 26, No. 20.

Agustin Palma et al., "Comparative study of the N-isobutyl-(2E,6Z)-dodecadienamide chemical and electrochemical syntheses", Green Chemistry 2009, pp. 283-293, vol. 11.

Philip E. Sonnet, "Synthesis of the N-Isobutylamide of All-trans-2,6,8,10-Dodecatetraenoic Acid", The Journal of Organic Chemistry, Apr. 1969, pp. 1147-1149, vol. 34, No. 4.

Martin Jacobson, "The Structure of Echinacein, the Insecticidal Component of American Coneflower Roots", The Journal of Organic Chemistry, May 1967, pp. 1646-1647, vol. 32, No. 5.

International Search Report for PCT/JP2011/077437 dated Feb. 7, 2012.

* cited by examiner

*Primary Examiner* — Porfirio Nazario Gonzalez
(74) *Attorney, Agent, or Firm* — Sughrue Mion, PLLC

(57) ABSTRACT

Provided are a method for producing a sanshool, which method has a short process and exhibits high stereoselectivity, as well as an iron carbonyl complex compound that is an intermediate useful for the production method.

A diene iron complex compound characterized by being represented by the following general formula (I):

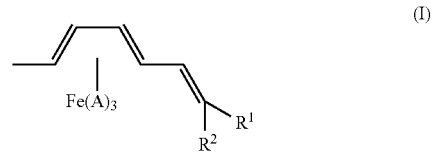

(I)

(in which A represents CO, $P(R^A)_3$, CN, NO, $SO(R^A)_3$, or $N(R^A)_2$; $R^A$ represents a straight chain or branched chain alkyl group having 1 to 4 carbon atoms or an aryl group having 6 to 12 carbon atoms; and one of $R^1$ and $R^2$ represents a hydrogen atom and the other one thereof represents a structure represented by the following formula (II)):

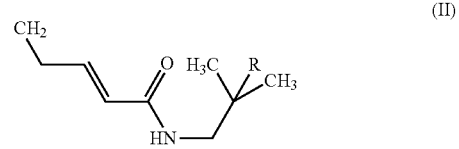

(II)

(in which R represents a hydrogen atom, a hydroxyl group, or a methyl group).

7 Claims, 1 Drawing Sheet

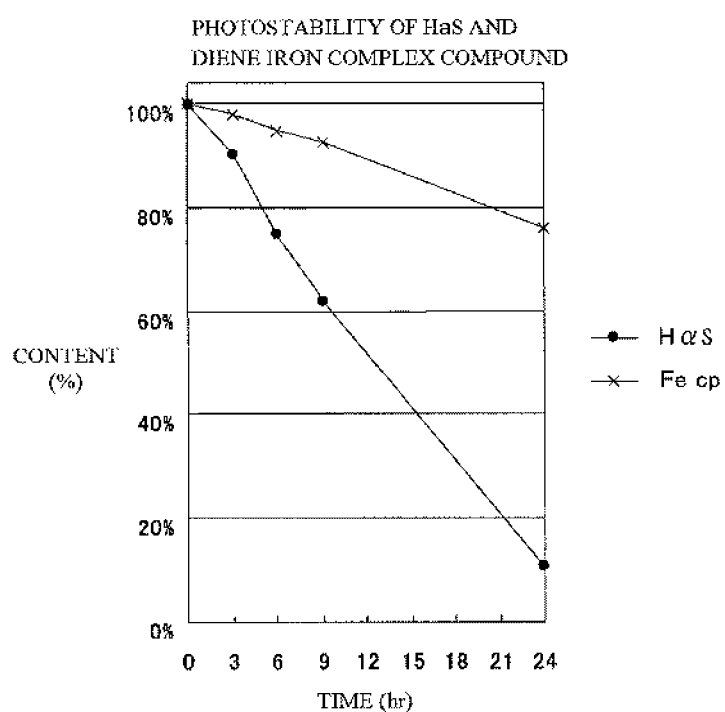

METHOD FOR PRODUCING SANSHOOL

TECHNICAL FIELD

The present invention relates to a method for producing a sanshool and to a diene iron complex compound that is an intermediate useful for the production method. In particular, the invention relates to a method for producing a sanshool, which can produce a sanshool in a short process and with high stereoselectivity, as well as to a novel diene iron complex compound that is an intermediate useful for the production method.

BACKGROUND ART

Sanshools are a main ingredient of a crude drug, "Zanthoxylum Fruit". In recent years, HαS (hydroxy-α-sanshool) has been reported to have effects such as stimulations of TRPV1 and TRPA1 and is now in the spotlight of the medicinal chemical field.

Sanshools including HαS have an unstable structure due to a triene moiety. Therefore, it has been difficult to constantly produce and supply sanshool as a pure substance. Conventionally, sanshools have been isolated and purified from an extract of sanshoo as a raw material by silica gel and ODS column chromatography.

Total syntheses of HαS and HβS (hydroxy-β-sanshool) have not been reported in the past, but a total synthesis of α-sanshool as an analogue thereof has been reported (see Non-Patent Documents 1 and 2). Methods described in the Non-Patent Documents 1 and 2 are both those for forming a triene moiety by a Wittig reaction.

RELATED ART DOCUMENTS

Non-Patent Documents

Non-Patent Document 1: Sonnet P. E., J. Org. Chem., 34, 1147-1149 (1969).
Non-Patent Document 2: Crombie L., Fisher D., Tetrahedron Lett., 26, 2481-2484 (1985).

SUMMARY OF THE INVENTION

Problems to be Solved by the Invention

However, the methods described in Non-Patent Documents 1 and 2 have showed low yield and low E/Z selectivity and thus can hardly be said to be practical synthesis methods.

Therefore, it is an object of the present invention to provide a method for producing a sanshool, which can produce a sanshool in a short process and with high stereoselectivity, as well as a novel diene iron complex compound that is a stable intermediate useful for the production method.

Means for Solving the Problems

The present inventors conducted extensive and intensive research to solve the above problems and found that the problems can be solved by using a specific novel diene iron complex compound, thereby completing the present invention.

A diene iron complex compound according to the present invention and a method for producing a sanshool according to the present invention are described in the following [1] to [7].

[1] A diene iron complex compound characterized by being represented by the following general formula (I):

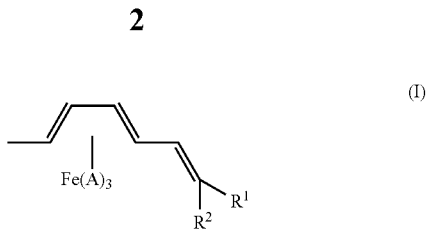

(in which A represents CO, $P(R^4)_3$, CN, NO, $SO(R^4)_3$, or $N(R^4)_2$; $R^4$ represents a straight chain or branched chain alkyl group having 1 to 4 carbon atoms or an aryl group having 6 to 12 carbon atoms; and one of $R^1$ and $R^2$ represents a hydrogen atom and the other one thereof represents a structure represented by the following formula (II)):

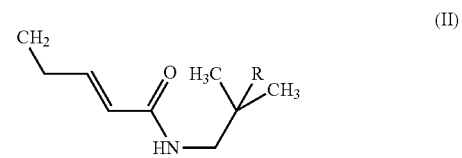

(in which R represents a hydrogen atom, a hydroxyl group, or a methyl group).

[2] A diene iron complex compound characterized by being represented by the following general formula (III):

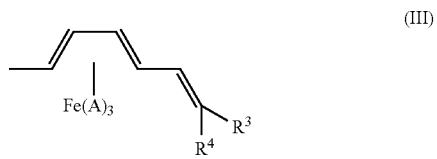

(in which A represents CO, $P(R^4)_3$, CN, NO, $SO(R^4)_3$, or $N(R^4)_2$; $R^4$ represents a straight chain or branched chain alkyl group having 1 to 4 carbon atoms or an aryl group having 6 to 12 carbon atoms; and one of $R^3$ and $R^4$ represents a hydrogen atom and the other one thereof represents a 2-cyanoethyl group).

[3] A method for producing a sanshool, characterized by reacting a diene iron complex compound represented by the following general formula (I):

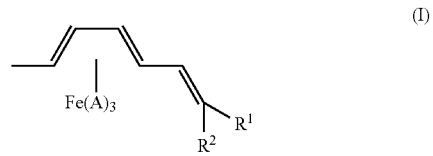

(in which A represents CO, $P(R^4)_3$, CN, NO, $SO(R^4)_3$, or $N(R^4)_2$; $R^4$ represents a straight chain or branched chain alkyl group having 1 to 4 carbon atoms or an aryl group having 6 to 12 carbon atoms; and one of $R^1$ and $R^2$ represents a hydrogen atom and the other one thereof represents a structure represented by the following formula (II)):

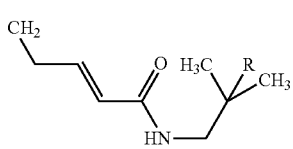

(II)

(in which R represents a hydrogen atom, a hydroxyl group, or a methyl group) with a deprotecting agent.

[4] The method for producing a sanshool according to [3], in which the deprotecting agent is one selected from the group consisting of cerium (IV) compounds, trimethylamine N-oxide, pyridine N-oxide, iron (III) chloride, copper (II) chloride, dichlorodicyano benzoquinone, and hydrogen peroxide.

[5] The method for producing a sanshool according to [3], further including:

a step of reducing a diene iron complex compound represented by the following general formula (III):

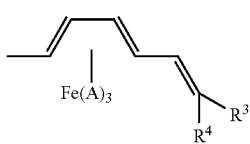

(III)

(in which A represents CO, $P(R^A)_3$, CN, NO, $SO(R^A)_3$, or $N(R^A)_2$; $R^A$ represents a straight chain or branched chain alkyl group having 1 to 4 carbon atoms or an aryl group having 6 to 12 carbon atoms; and one of $R^3$ and $R^4$ represents a hydrogen atom and the other one thereof represents a 2-cyanoethyl group) to an aldehyde compound; and a step of reacting the obtained aldehyde compound with dimethyl(isobutylcarbamoyl)methylphosphonate or diethyl (isobutylcarbamoyl)methylphosphonate to obtain the diene iron complex compound represented by the general formula (I).

[6] The method for producing a sanshool according to [3], further including:

a step of reducing a diene iron complex compound represented by the following general formula (III)

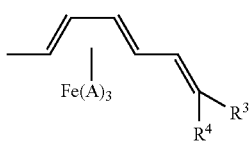

(III)

(in which A represents CO, $P(R^A)_3$, CN, NO, $SO(R^A)_3$, or $N(R^A)_2$; $R^A$ represents a straight chain or branched chain alkyl group having 1 to 4 carbon atoms or an aryl group having 6 to 12 carbon atoms; and one of $R^3$ and $R^4$ represents a hydrogen atom and the other one thereof represents a 2-cyanoethyl group) to an aldehyde compound;

a step of reacting the obtained aldehyde compound with diethylphosphonoacetic acid to obtain a diene iron complex compound represented by the following general formula (VII):

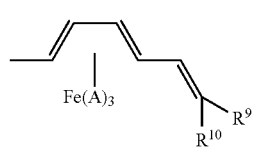

(VII)

(in which A represents CO, $P(R^A)_3$, CN, NO, $SO(R^A)_3$, or $N(R^A)_2$; $R^A$ represents a straight chain or branched chain alkyl group having 1 to 4 carbon atoms or an aryl group having 6 to 12 carbon atoms; and one of $R^9$ and $R^{10}$ represents a hydrogen atom and the other one thereof represents a structure represented by the following formula (VIII)),

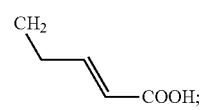

(VIII)

and a step of reacting the obtained diene iron complex compound represented by the general formula (VII) with an amine represented by the following general formula (IX):

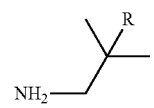

(IX)

(in which R represents a hydrogen atom, a hydroxyl group, or a methyl group) to obtain the diene iron complex compound represented by the general formula (I).

[7] The method for producing a sanshool according to [3], further including:

a step of reacting a compound represented by the following formula (X):

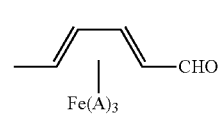

(X)

with 4-(1-phenyl-1H-tetrazole-5-ylsulfonyl)butanenitrile to obtain a diene iron complex compound represented by the following general formula (III):

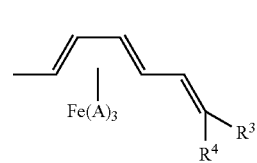

(III)

(in which A represents CO, $P(R^A)_3$, CN, NO, $SO(R^A)_3$, or $N(R^A)_2$; $R^A$ represents a straight chain or branched chain alkyl group having 1 to 4 carbon atoms or an aryl group having 6 to 12 carbon atoms; and one of $R^3$ and $R^4$ represents a hydrogen atom and the other one thereof represents a 2-cyanoethyl group);

a step of reducing the diene iron complex compound represented by the general formula (III) to an aldehyde compound;

a step of reacting the obtained aldehyde compound with diethylphosphonoacetic acid to obtain a diene iron complex compound represented by the following general formula (VII):

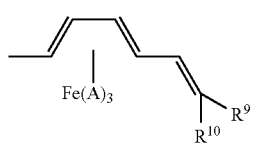
(VII)

(in which A represents CO, $P(R^4)_3$, CN, NO, $SO(R^4)_3$, or $N(R^4)_2$; $R^4$ represents a straight chain or branched chain alkyl group having 1 to 4 carbon atoms or an aryl group having 6 to 12 carbon atoms; and one of $R^9$ and $R^{10}$ represents a hydrogen atom and the other one thereof represents a structure represented by the following formula (VIII)):

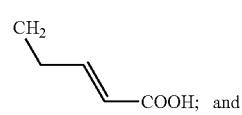
(VIII)

and a step of reacting the obtained diene iron complex compound represented by the general formula (VII) with an amine represented by the following general formula (IX):

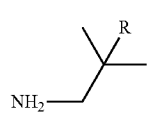
(IX)

(in which R represents a hydrogen atom, a hydroxyl group, or a methyl group) to obtain the diene iron complex compound represented by the general formula (I).

Advantages of the Invention

According to the present invention, there can be provided the method for producing a sanshool, which can produce a sanshool in a short process and with high stereoselectivity, as well as the diene iron complex compound that is an intermediate useful for the production method.

BRIEF DESCRIPTION OF THE DRAWING

FIG. 1 depicts a graph illustrating time-related deterioration of contents (represented by %) of hydroxy-α-sanshool (HαS) and a diene iron complex compound (compound 5, designated as Fe cp) in sample solutions under light exposure in Experiment Example 9.

MODES FOR CARRYING OUT THE INVENTION

Hereinbelow, embodiments of the present invention will be described in detail.

[Diene Iron Complex Compound]

A diene iron complex compound according to the present invention is represented by the following general formula (I):

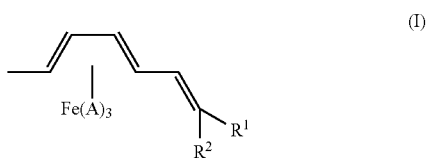
(I)

(in which A represents CO, $P(R^4)_3$, CN, NO, $SO(R^4)_3$, or $N(R^4)_2$; $R^4$ represents a straight chain or branched chain alkyl group having 1 to 4 carbon atoms or an aryl group having 6 to 12 carbon atoms; and one of $R^1$ and $R^2$ represents a hydrogen atom and the other one thereof represents a structure represented by the following formula (II)):

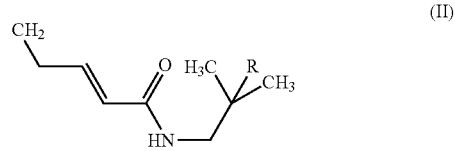
(II)

(in which R represents a hydrogen atom, a hydroxyl group, or a methyl group).

Examples of the straight chain or branched chain alkyl group having 1 to 4 carbon atoms represented by the $R^4$ include a methyl group, an ethyl group, a propyl group, an isopropyl group, a butyl group, a t-butyl group, and the like, and preferred is a methyl group. Additionally, examples of the aryl group having 6 to 12 carbon atoms include a phenyl group, a 2-pyridyl group, a 3-pyridyl group, a 4-pyridyl group, a 2-thienyl group, a 3-thienyl group, and the like, and preferred is a phenyl group.

By reacting the above diene iron complex compound with a deprotecting agent, a sanshool such as α-sanshool, β-sanshool, or hydroxy-α-sanshool can be conveniently produced. Examples of the deprotecting agent include cerium (IV) compounds such as cerium ammonium nitrate (CAN), trimethylamine N-oxide, pyridine N-oxide, iron ((III) chloride, copper (II) chloride, dichlorodicyano benzoquinone, hydrogen peroxide, and the like, among which cerium (IV) compounds, trimethylamine N-oxide, and pyridine N-oxide are suitable. Most preferable is trimethylamine N-oxide that can produce sanshools with less by-products.

In addition, the sanshools are unstable, and particularly, in hydroxy-α-sanshool, decomposition (isomerization or the like) occurs markedly under light exposure. However, the diene iron complex compound of the present invention described above is relatively stable and hardly causes isomerization or the like due to light. Therefore, the sanshools can be produced by preserving the diene iron complex compound of the present invention and performing deprotection reaction when needed.

Another diene iron complex compound according to the present invention is represented by the following general formula (III):

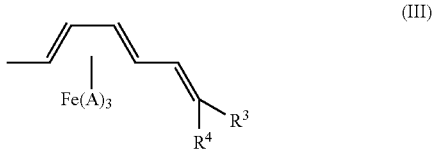
(III)

(in which A represents CO, P(R$^A$)$_3$, CN, NO, SO(R$^A$)$_3$, or N(R$^A$)$_2$; R$^A$ represents a straight chain or branched chain alkyl group having 1 to 4 carbon atoms or an aryl group having 6 to 12 carbon atoms; and one of R$^3$ and R$^4$ represents a hydrogen atom and the other one thereof represents a 2-cyanoethyl group).

The diene iron complex compound represented by the general formula (III) serves as a raw material in a method for producing a sanshool, which can produce conveniently a sanshool in a short process, by the following reaction. Depending on the use of either a diene iron complex compound in which R$^3$ represents a 2-cyanoethyl group or a diene iron complex compound in which R$^4$ represents a 2-cyanoethyl group, either an alpha form or beta form of sanshool can be arbitrarily produced.

As an example of the diene iron complex compound represented by the general formula (III), a compound, for example, in which A represents CO in the formula can be synthesized by a Wittig reaction or the like from a compound 1 represented by the following formula:

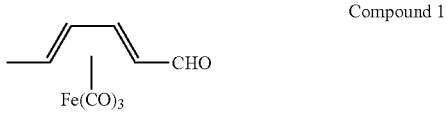
Compound 1

In addition, different geometric isomers may be formed by using different reactions such as a Wittig reaction, a Horner-Wadsworth-Emmons reaction, and a Julia-Lythgoe olefination.

The Wittig reaction can be performed, for example, with reference to methods described in literature such as Wittig, G; Schollkopf, U. Ber., 1954, 87, 1318., and Maryanoff, B. E. et al. Chem. Rev. 1989, 89, 863.

The Horner-Wadsworth-Emmons reaction can be performed, for example, with reference to methods described in literature such as Homer, L.; Hoffmann, H. M. R.; Wippel, H. G; Klahre, G Ber., 1959, 92, 2499., Maryanoff, B. E.; Reitz, A. B. Chem. Rev. 1989, 89, 863., and Kelly, S. E. Comprehensive Organic Synthesis 1991, 1, 729.

The Julia-Lythgoe olefination can be performed, for example, with reference to methods described in literature such as Julia, M; Paris, J. M. Tetrahedron Lett., 1973, 4833., and Blakemore, P. R JCS Perkin Trans., 1, 2002, 2563.

In addition, the above compound 1 can be easily synthesized, for example, by heating and stirring 2,4-hexadienal easily obtainable as a commercially available reagent and an iron complex such as Fe$_3$(CO)$_{12}$.

[Method for Producing Sanshool]

A method for producing a sanshool according to the present invention is characterized by reacting the diene iron complex compound represented by the general formula (I) with a deprotecting agent. Examples of the deprotecting agent include cerium (IV) compounds such as cerium ammonium nitrate (CAN), trimethylamine N-oxide, pyridine N-oxide, iron (III) chloride, copper (II) chloride, dichlorodicyano benzoquinone, hydrogen peroxide, and the like, among which cerium (IV) compounds, trimethylamine N-oxide, and pyridine N-oxide are suitable, and most preferable is trimethylamine N-oxide that can produce sanshools with less by-product formation.

The temperature for the reaction with a deprotecting agent is not particularly limited, and preferably, the reaction is performed at −20 to 50° C. In addition, preferably, the reaction is performed within 1 hour.

Another method for producing a sanshool according to the present invention is characterized by including:

a step (A) of reducing the diene iron complex compound represented by the general formula (III) to an aldehyde compound;

a step (B) of reacting the obtained aldehyde compound with dimethyl(isobutylcarbamoyl)methylphosphonate or diethyl(isobutylcarbamoyl)methylphosphonate to obtain the diene iron complex compound represented by the general formula (IV); and a step (C) of reacting the obtained diene iron complex compound represented by the general formula (IV) with a deprotecting agent.

<Step (A)>

An example of the reaction of the above step (A) can be represented by the following formula. The following reaction formula corresponds to a case of using, among diene iron complex compounds represented by the general formula (III), a diene iron complex compound in which A represents CO and R$^4$ represents a 2-cyanoethyl group.

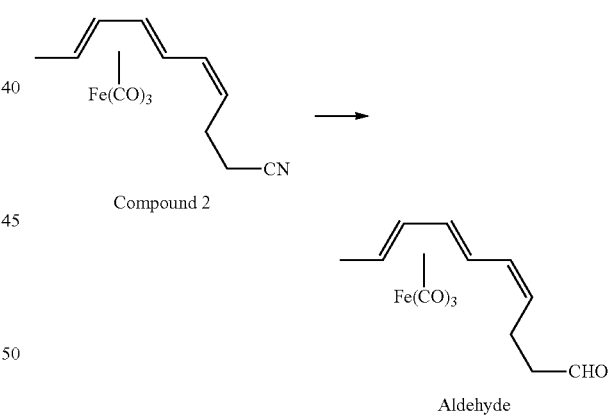
Compound 2

Aldehyde

Examples of a reducing agent include lithium tri(ethoxy) aluminium hydride, lithium tri(sec-butyl)borohydride, diisobutylaluminium hydride (DIBAL-H), and the like, among which preferable is DIBAL-H. An example of a suitable reaction format is to perform a reduction reaction using DIBAL-H in an amount of 1.0 to 2.0 equivalents with respect to the diene iron complex compound represented by the general formula (III), while cooling to a temperature of −80 to −20° C. in an organic solvent such as toluene.

<Step (B)>

An example of the reaction of the above step (B) can be represented by the following formula:

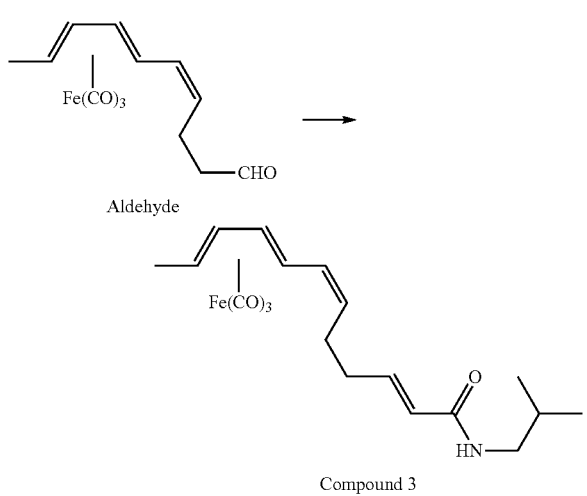

Aldehyde

Compound 3

Together with the above compound 3, there may be obtained an isomer (3-geo) derived from an enamide double bond, represented by a formula below. However, preferably, the amount of the isomer is minimum. The isomer represented by the formula below can be easily separated, for example, by silica gel column chromatography. Furthermore, recrystallization of the above compound 3 can increase the purity.

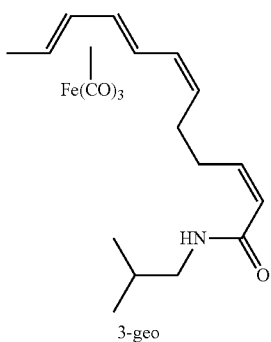

3-geo

<Step (C)>

The step of reacting the diene iron complex compound represented by the general formula (IV) with a deprotecting agent is the same as that described above.

A still another method for producing a sanshool according to the present invention is a method for producing a sanshool represented by the general formula (VI), the method being characterized by including:

a step (D) of reducing the diene iron complex compound represented by the general formula (III) to an aldehyde compound;

a step (E) of reacting the obtained aldehyde compound with diethylphosphonoacetic acid to obtain the diene iron complex compound represented by the general formula (VII);

a step (F) of reacting the obtained diene iron complex compound represented by the general formula (VII) with the amine represented by the general formula (IX) to obtain a condensate; and a step (G) of reacting the obtained condensate with a deprotecting agent.

<Step (D)>

An example of the reaction of the above step (D) can be represented by the following formula. The following reaction formula corresponds to a case of using, among diene iron complex compounds represented by the general formula (III), a diene iron complex compound in which A represents CO and $R^4$ represents a 2-cyanoethyl group.

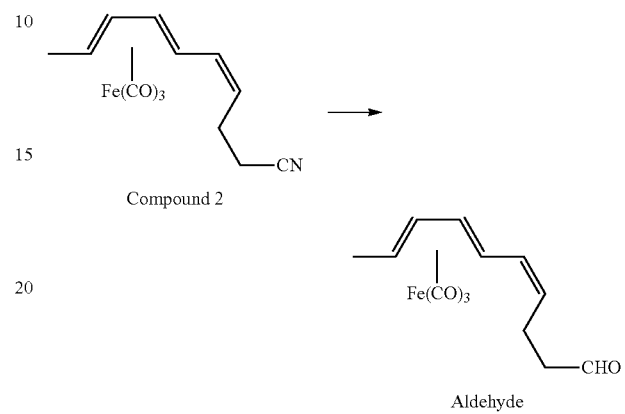

Compound 2

Aldehyde

The above step (D) can be performed in the same manner as the above step (A).

<Step (E)>

An example of the reaction of the above step (E) can be represented by the following formula. The following reaction formula corresponds to the case of using, among diene iron complex compounds represented by the general formula (III), a diene iron complex compound in which $R^4$ represents a 2-cyanoethyl group.

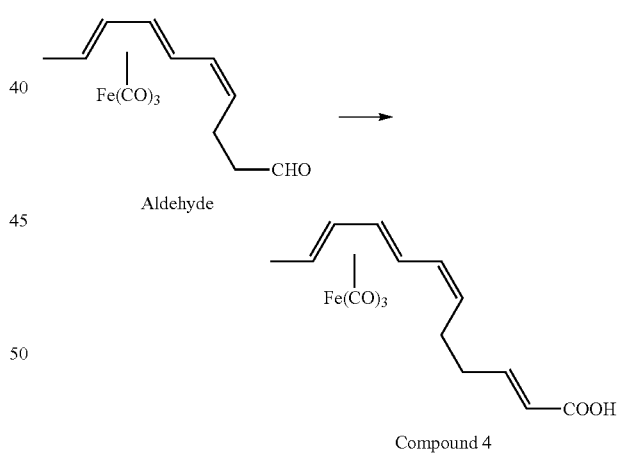

Aldehyde

Compound 4

The step (E) can be performed, for example, by a Honor-Wadsworth-Emmons reaction, a Knoevenagel condensation, or the like using diethylphosphonoacetic acid according to the Schauer method.

The Knoevenagel condensation may be performed, for example, with reference to a method described in literature such as Jones, G. Org. React. 1967, 15, 204., or Tietze, L. F.; Beifuss, U. Comprehensive Organic Synthesis 1991, 2, 341.

<Step (F)>

An example of the reaction of the above step (F) can be represented by the following formula. The following reaction formula corresponds to the case of using, among diene iron complex compounds represented by the general formula (III), a diene iron complex compound in which R⁴ represents a 2-cyanoethyl group.

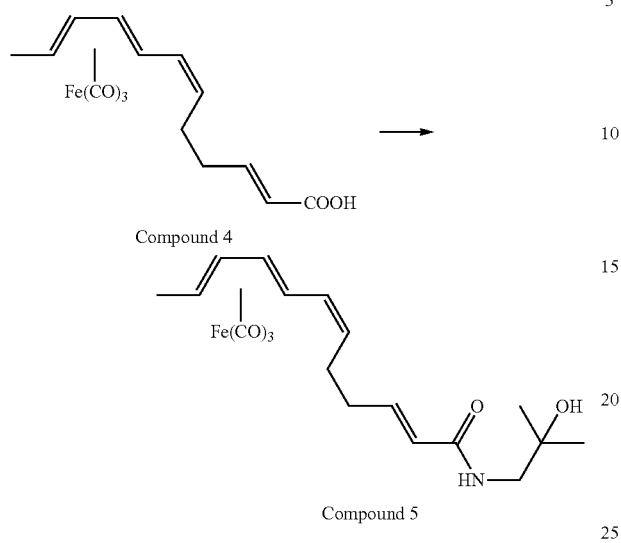

Compound 4

Compound 5

The step (F) may be performed by a common amidation reaction, but is preferably performed by a condensation reaction with the amine using N-methyl-2-chloropyridium iodide or by a condensation reaction using a combination of a water-soluble condensing agent such as a water-soluble carbodiimide (1-ethyl-3-(3-dimethylaminopropyl)carbodiimide hydrochloride or the like) and hydroxybenzotriazole (HOBt).

In addition, the amine represented by the general formula (IX) can be synthesized by a known method. For example, among the amines, an amine in which R represents a hydroxy group, namely, 2-hydroxy-2-methylpropylamine can be obtained by reacting benzylamine in an amount of 1.1 equivalent with respect to 1,2-epoxy-2-methylpropane (EMP) and then performing deprotection through catalytic hydrogenation reaction. The above reaction can be performed, for example, with reference to a method described in Candice Menzzi-Smarrito et al., J. Agric. Food Chem. 57, 1982 (2009).

<Step (G)>

The step of reacting the condensate obtained in the above step (F) with a deprotecting agent may be performed in the same manner as the method of reacting the diene iron complex compound represented by the general formula (I) with a deprotecting agent.

<Step (H)>

As an example of the diene iron complex compound represented by the general formula (III), a compound, for example, in which A represents CO in the formula can be synthesized also by a Julia-Kocienski olefination reaction using 4-(1-phenyl-1H-tetrazole-5-ylsulfonyl)butanenitrile from the compound 1 represented by the following formula:

Compound 1

The Julia-Kocienski olefination reaction can be performed, for example, with reference to a method described in literature such as P. J. Kocienski, et al., Synlett, 1998, 26. With this reaction, among diene iron complex compounds represented by the general formula (III), a diene iron complex compound in which R³ represents a 2-cyanoethyl group (that is, a compound having an E,E,E-triene skeleton) can be selectively synthesized.

After that, using the obtained diene iron complex compound represented by the general formula (III), by going through the above-described steps (D), (E), (F), and (G), β-sanshool can be produced.

EXAMPLES

Experiment Example 1

Synthesis of tricarbonyl[(2,3,4,5-η)-(2E,4E)-hexa-2,4-dienal]iron

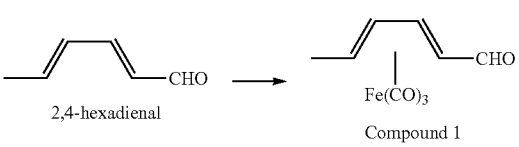

2,4-hexadienal

Compound 1

At room temperature, 2,4-hexadienal (1.81 mL) was added in a solution of $Fe_3(CO)_{12}$ (5.7 g) suspended in toluene (30 mL), and the mixed solution was stirred at 60° C. for 24 hours. Then, the reaction solution was stirred at 80° C. for 1 hour. The reaction solution was purified by silica gel chromatography (hexane→hexane/ethyl acetate=10:1) to obtain a roughly purified product. The obtained roughly purified product was dried under vacuum to obtain 2.84 g (a yield of 70.8%) of oily tricarbonyl[2,3,4,5-η]-(2E,4E)-hexa-2,4-dienal]iron.

Data of the obtained compound are as follows:

¹H-NMR (CDCl₃, 400 MHz) δ: 1.26 (1H, dd, J=4.4, 8.3 Hz), 1.51 (3H, d, J=6.1 Hz), 1.70 (1H, dq, J=8.7, 6.1 Hz), 5.30 (1H, dd, J=5.1, 8.7 Hz), 5.77 (1H, dd, J=5.1, 8.3 Hz), 9.26 (1H, d, J=4.4 Hz);

ESI-LRMS: m/z: +ESI 259 [M+Na]⁺, 237 [M+H]⁺, −ESI 235 [M−H]⁻;

ESI-HRMS: m/z: 258.9666 (Calcd for $C_9H_8O_4FeNa$: 258.9670).

Experiment Example 2-1

Synthesis of tricarbonyl[(6,7,8,9-η)-(4Z,6E,8E)-deca-4,6,8-trienenitrile]iron

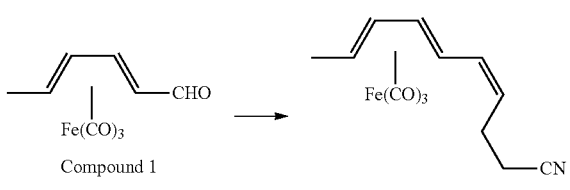

Compound 1

Compound 2

1) A mixed solution of 3-cyanopropyltriphenylphosphonium bromide ($PPh_3P^+(CH_2)_3CN\,Br^-$) (12.3 g, 30.0 mol) and THF (30 mL) was cooled to 0° C. in an ice water bath. To the cooled solution was added sodium hexamethyldisilazide (NaHMDS) (1.0 mol/L) suspended in THF (30 mL). The obtained red-orange colored solution was stirred for 30 minutes. After removing the ice bath and stopping the stirring, the resulting solution was allowed to stand for approximately 1 hour until NaBr was completely precipitated to be separated, thereby obtaining a ylide solution.

2) To a solution of tricarbonyl[(2,3,4,5-η)-(2E,4E)-hexa-2,4-dienal]iron (4.20 g) dissolved in THF (35 mL) was added dropwise 0.5 mol/L of the above ylide solution (60.0 mL) at −78° C. under an argon atmosphere. After that, the reaction solution was stirred at −78° C. for 1 hour. While gradually increasing the temperature of the reaction solution, the solution was stirred for 1.5 hours and the temperature thereof was increased to −20° C. Next, a saturated ammonium chloride aqueous solution was added and the water layer was extracted with ethyl acetate. The organic layer was washed with a saturated saline solution and dried over anhydrous sodium sulfate. The organic solvent was removed under vacuum, and then, the residue was purified by silica gel chromatography (hexane/ethyl acetate=5:1) to obtain 4.61 g (a yield of 90.4%) of tricarbonyl[(6,7,8,9-η)-(4Z,6E,8E)-deca-4,6,8-trienenitrile]iron.

Data of the obtained compound are as follows:

$^1$H-NMR (CDCl$_3$, 400 MHz) δ: 1.42-1.45 (4H, m), 1.75 (1H, dd, J=9.6, 10.7 Hz), 2.36-2.47 (4H, m), 5.07 (1H, dd, J=4.9, 7.3 Hz), 5.19 (1H, dd, J=4.9, 8.2 Hz), 5.32 (1H, td, J=7.3, 10.7 Hz), 5.54 (1H, t, J=10.7 Hz);

$^{13}$C-NMR (CDCl$_3$, 100 MHz) δ: 17.05, 19.18, 23.83, 54.48, 57.60, 82.40, 85.97, 119.13, 125.14, 134.15, 212.05;

ESI-MS m/z: +ESI 310 [M+Na]$^+$, 288 [M+H]$^+$, −ESI 286 [M−H]$^-$;

HRESI-MS m/z: 310.0143 (Calcd for C$_{13}$H$_{13}$NO$_3$FeNa: 310.0143);

IR (KBr): cm$^{-1}$: 2033, 1952, 625, 568.

Experiment Examples 2-2 to 2-5

Reaction was performed in the same manner as the above Experiment Example 2-1 except that the base, the solvent, and the temperature to be used were changed to those shown in Table 1 below. Table 1 below shows yields of tricarbonyl [(6,7,8,9-η)-(4Z,6E,8E)-deca-4,6,8-trienenitrile]iron.

TABLE 1

| | Base (solvent) | Temperature of 1) | Solvent of 2) | Temperature of 2) | Yield (%) |
|---|---|---|---|---|---|
| Experiment Example 2-1 | NaHMDS (THF) | 0° C.→r.t. | THF | −78° C.→−20° C. | 90.4 |
| Experiment Example 2-2 | n-BuLi, HMPA (THF) | 0° C. | THF | −78° C.→0° C. | 27.9 |
| Experiment Example 2-3 | t-BuOK (DMSO-THF) | r.t. | THF | −20° C. | 17.1 |
| Experiment Example 2-4 | NaH (DMSO-THF) | 0° C. | THF | 0° C. | 54.7 |
| Experiment Example 2-5 | NaH (DMSO) | r.t. | DMSO | r.t. | 20.6 |

Experiment Example 3

Preparation of diethyl(isobutylcarbamoyl)methylphosphonate

Diethylphosphonoacetic acid (1.29 mL) was dissolved in dichloromethane (20 mL), and to the mixed solution was added dropwise (COCl)$_2$ (2.90 mL) at room temperature under an argon atmosphere. The resulting solution was stirred for 16 hours. The mixture product was dried and concentrated under vacuum to obtain an oily acid chloride. To a solution of the acid chloride dissolved in diethyl ether (20.0 mL) was added isobutylamine (1.60 mL) at 0° C. under an argon atmosphere, and the mixed solution was stirred at 0° C. Subsequently, the mixed solution was stirred at room temperature for 5 hours. Precipitated salt was removed by filtration, and the resulting solution was concentrated under vacuum. To the concentrated solution was added 1 mol/L hydrochloric acid and the water phase was extracted with ethyl acetate. The organic phase was washed with a saturated sodium hydrogen carbonate aqueous solution, dried over anhydrous sodium sulfate, and then dried under vacuum at room temperature to obtain 1.17 g of diethyl(isobutylcarbamoyl)methylphosphonate.

Data of the obtained compound are as follows:

$^1$H-NMR (CDCl$_3$, 400 MHz) δ: 0.93 (6H, d, J=6.6 Hz), 1.34 (6H, t, J=7.1 Hz), 1.82 (1H, m), 2.87 (2H, d, J=20.5 Hz), 3.11 (2H, t, J=6.3 Hz), 4.11-4.23 (4H, m), 6.88 (1H, brs).

Experiment Example 4-1

Synthesis of tricarbonyl[(8,9,10,11-η)-(2E,6Z,8E, 10E)-N-isobutyltetradeca-2,6,8,10-tetraenamide]iron

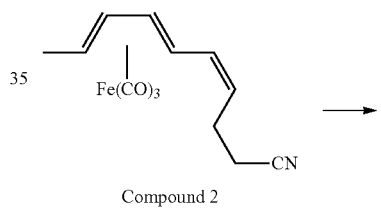

Compound 2

-continued

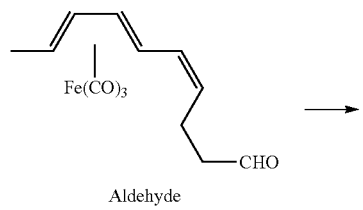

Aldehyde

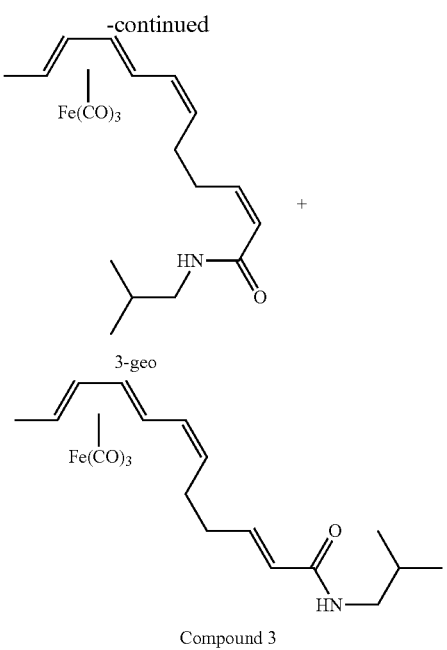

Compound 3

1) To a toluene solution (2.0 mL) of tricarbonyl[(6,7,8,9-η)-(4Z,6E,8E)-deca-4,6,8-trienenitrile]iron (143.7 mg) was added dropwise DIBAL-H (0.7 mL) at −20° C. under an argon atmosphere. The reaction solution was stirred at −20° C. for 1 hour. To the reaction solution was added 1 mol/L hydrochloric acid, and the mixed solution was stirred for 5 minutes. Then, the water phase was extracted with ethyl acetate. The organic phase was washed with a saturated saline solution and dried over anhydrous sodium sulfate. The organic solvent was removed by drying under vacuum to obtain 143.7 mg of an aldehyde compound.

2) To a mixed solution of diethyl(isobutylcarbamoyl)methylphosphonate (130.5 mg), TMEDA (tetramethylethylenediamine) (0.09 mL), TEA (triethylamine) (0.16 mL), and the above aldehyde compound dissolved in THF (1.5 mL) was added dropwise $Zn(OTf)_2$ (zinc triflate) (226.2 mg). Then, the mixed solution was stirred at room temperature for 15 hours. To the obtain reaction solution was added 1 mol/L hydrochloric acid and the water phase was extracted with ethyl acetate. The organic phase was washed with a saturated sodium hydrogen carbonate aqueous solution and dried over anhydrous sodium sulfate. The organic solvent was removed under vacuum and the resulting residue was purified by silica gel chromatography (ethyl acetate/hexane=2/1) to obtain tricarbonyl[(8,9,10,11-η)-(2E,6Z,8E,10E)-N-isobutyltetradeca-2,6,8,10-tetraenamide]iron (118.6 mg) as a yellow viscous oily product. The obtained compound was recrystallized from an ether/hexane solvent to obtain a light yellow solid, which was then dried under vacuum at room temperature (96.1 mg).

Data of the obtained compound are as follows:

$^1$H-NMR (CDCl$_3$, 400 MHz) δ: 0.93 (6H, d, J=6.6 Hz), 1.36 (1H, m), 1.43 (3H, d, J=5.8 Hz), 1.80 (1H, m), 1.87 (1H, dd, J=8.8, 10.5 Hz), 2.23-2.32 (4H, m), 3.16 (2H, d, J=6.6 Hz), 5.04 (1H, dd, J=4.9, 8.0 Hz), 5.16 (1H, dd, J=4.9, 8.8 Hz), 5.32 (1H, td, J=6.6, 10.5 Hz), 5.42 (1H, t, J=10.5 Hz), 5.42 (1H, brs), 5.84 (1H, d, J=15.1 Hz), 6.82 (1H, td, J=6.6, 15.1 Hz); $^{13}$C-NMR (CDCl$_3$, 100 MHz), δ: 19.15, 20.11, 26.58, 28.58, 31.48, 46.86, 56.13, 57.17, 82.23, 85.53, 124.28, 129.31, 131.62, 143.24, 165.87, 212.36;

ESI-MS m/z: +ESI 410 [M+Na]$^+$, 388 [M+H]$^+$, −ESI 386 [M−H]$^−$;

HRESI-MS m/z: 410.1034 (Calcd for $C_{19}H_{25}NO_4FeNa$: 410.1031);

IR (KBr): cm$^{-1}$: 3270, 2048, 1988, 1970, 1954, 1675, 1618, 1549, 563.

Experiment Examples 4-2 to 4-4

Reaction was performed in the same manner as the Experiment Example 4-1, except that the base and temperature to be used were changed to those shown in Table 2 below. Table 2 below shows yields of the tricarbonyl[(8,9,10,11-η)-(2E,6Z,8E,10E)-N-isobutyltetradeca-2,6,8,10-tetraenamide]iron (designated as 3). 3-geo represents a geometrical isomer of the 3. In addition, the isomer was able to be easily separated in a silica gel column. Furthermore, 3 with high purity was able to be obtained by recrystallization.

TABLE 2

| | | Yield (%)* | |
| --- | --- | --- | --- |
| | Reaction conditions | 3-geo | 3 |
| Experiment Example 4-1 | 1) DIBAL-H, toluene, −20° C., 1 h<br>2) Diethyl(isobutylcarbamoyl)methylphosphonate, Zn(OTf)$_2$, TEA, TMEDA, THF, r.t., 15 h | ** | 61.3 |
| Experiment Example 4-2 | 1) DIBAL-H, toluene, −20° C., 1 h<br>2) Diethyl(isobutylcarbamoyl)methylphosphonate, NaHMDS, THF, −10° C., 0.5 h | 11.7 | 57.4 |
| Experiment Example 4-3 | 1) DIBAL-H, toluene 1, −20° C., 1 h<br>2) Diethyl(isobutylcarbamoyl)methylphosphonate, DIEA, LiCl, DBU, THF, −30° C.→r.t., 2 h | 13.9 | 47.1 |
| Experiment Example 4-4 | 1) DIBAL-H, toluene, −20° C., 1 h<br>2) Diethyl(isobutylcarbamoyl)methylphosphonate, NaH, THF, r.t., 2 h | 9.9 | 53.7 |

*Isolation yield
**Trace

Experiment Example 5-1

Synthesis of (2E,6Z,8E,10E)-N-isobutyldodeca-2,6,8,10-tetraenamide (α-sanshool)

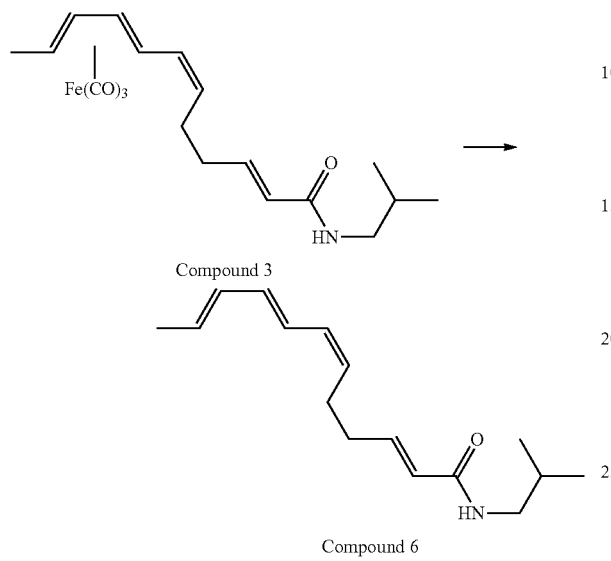

Compound 3

Compound 6

To a mixture product of tricarbonyl[(8,9,10,11-η)-(2E,6Z,8E,10E)-N-isobutyldodeca-2,6,8,10-tetraenamide]iron (96.1 mg) and trimethylamine-N-oxide (194.0 mg) was added acetonitrile (2.0 mL) at room temperature under an argon atmosphere. The mixed solution was stirred for 1.5 hours. Then, water was added to the reaction solution to extract the water phase with ethyl acetate. The organic phase was dried over anhydrous sodium sulfate. The organic solvent was removed under vacuum. The mixture product was filtered through a cotton plug and evaporated to obtain a light yellow amorphous solid (60.6 mg).

Data of the obtained compound are as follows:

$^1$H-NMR (CDCl$_3$, 400 MHz) δ: 0.93 (6H, d, J=6.6 Hz), 1.78 (3H, d, J=6.6 Hz), 1.78 (1H, m), 2.24-2.37 (4H, m), 3.15 (2H, t, J=6.8 Hz), 5.37 (1H, td, J=7.5, 10.7 Hz), 5.42 (1H, brs), 5.73 (1H, qd, J=7.5, 13.8 Hz), 5.78 (1H, td, J=1.5, 15.1 Hz), 6.02 (1H, t, J=10.7 Hz), 6.13 (1H, dd, J=10.2, 13.8 Hz), 6.17 (1H, dd, J=10.2, 13.8 Hz), 6.33 (1H, dd, J=10.7, 13.8 Hz), 6.82 (1H, td, J=6.6, 15.1 Hz).

Experiment Example 5-2

Reaction was performed in the same manner as Experiment Example 5-1 except that CAN (ceric ammonium nitrate) was used instead of trimethylamine N-oxide; acetone was added instead of acetonitrile; and the time for stirring after that was changed from 1.5 hours to 15 minutes. Table 3 below shows the results.

TABLE 3

| | Reaction conditions | Yield (%) |
|---|---|---|
| Experiment Example 5-1 | Me$_3$NO (10 eq), MeCN, r.t, 1.5 h | 98.8 |
| Experiment Example 5-2 | 1 mol/L CANaq (3 eq), acetone, r.t., 15 min | 98.6 |

Experiment Example 6

Synthesis of tricarbonyl[(8,9,10,11-η)-(2E,6Z,8E,10E)-dodeca-2,6,8,10-tetraenoic acid]iron

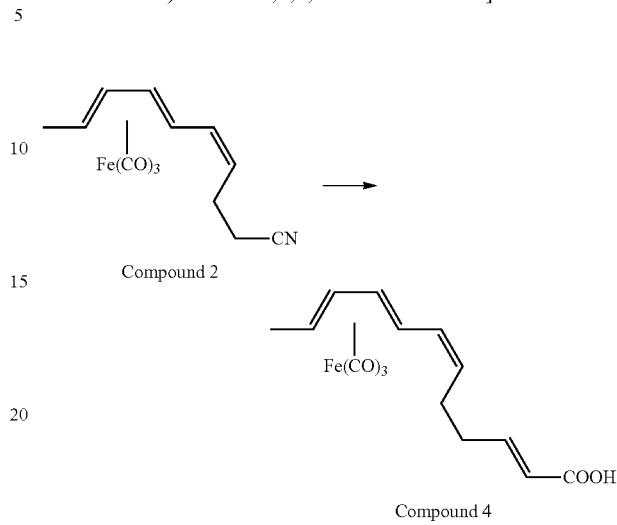

Compound 2

Compound 4

1) To a solution of tricarbonyl[(6,7,8,9-η)-(4Z,6E,8E)-deca-4,6,8-trienenitrile]iron (2.0 g) dissolved in toluene (50 mL) was added dropwise DIBAL-H (13.9 mL) at −20° C. under an argon atmosphere, and the mixed solution was stirred for 1 hour. To the reaction solution was added 1 mol/L hydrochloric acid and the water phase was extracted with ethyl acetate. The organic phase was washed with a saturated saline solution and dried over anhydrous sodium sulfate. The organic solvent was removed under vacuum to obtain an aldehyde compound.

2) To a solution of Zn(OTf)$_2$ (5.62 g), TMEDA (1.25 mL), and DBU (1,8-diazabicyclo[5,4,0]undeca-7-ene) (4.2 mL) dissolved in THF (20.0 mL) was added diethylphosphonoacetic acid (1.34 mL), and the mixed solution was stirred at room temperature for 2 hours. A solution of the above aldehyde compound dissolved in THF (20.0 mL) was added to the reaction solution, and the resulting solution was stirred at room temperature for 4 hours. After that, to the reaction solution was added 1 mol/L hydrochloric acid and the water phase was extracted with ethyl acetate. The organic phase was washed with a saturated saline solution and dried over anhydrous sodium sulfate. After removing the organic solvent under vacuum, the resulting residue was purified by silica gel chromatography (ethyl acetate/hexane=4/1→2/1) to obtain tricarbonyl[(8,9,10,11-η)-(2E,6Z,8E,10E)-dodeca-2,6,8,10-tetraenoic acid]iron (1.73 g).

Data of the obtained compound are as follows:

$^1$H-NMR (CDCl$_3$, 400 MHz) δ: 1.38-1.45 (4H, m), 1.89 (1H, dd, J=9.6, 10.6 Hz), 2.43 (2H, dd, J=7.3, 14.3 Hz), 2.56 (2H, m), 5.05 (1H, dd, J=4.6, 7.3 Hz), 5.15 (1H, dd, J=4.6, 8.5 Hz), 5.29 (1H, td, J=7.3, 10.6 Hz), 5.43 (1H, t, J=10.6 Hz), 9.80 (1H, s);

$^{13}$C-NMR (CDCl$_3$, 100 MHz), δ:19.15, 26.23, 31.79, 55.79, 57.18, 82.23, 85.58, 121.14, 128.59, 132.06, 150.90, 171.12, 212.26;

ESI-MS m/z: +ESI 355 [M+Na]$^+$, 333 [M+H]$^+$, −ESI 331 [M−H]$^-$;

HRESI-MSm/z: 355.0246 (Calcd for C$_{15}$H$_{16}$NO$_5$FeNa: 355.0245);

IR (film): cm$^{-1}$: 2036, 1964, 1696, 1652.

Experiment Example 7-1

Synthesis of tricarbonyl[(8,9,10,11-η)-(2E,6Z,8E,10E)-N-(2-hydroxy-2-methylpropyl)dodeca-2,6,8,10-tetraenamide]iron

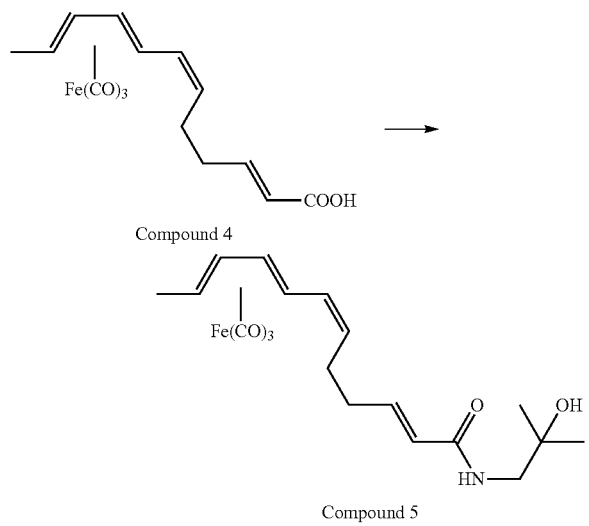

Tricarbonyl[(8,9,10,11-η)-(2E,6Z,8E,10E)-dodeca-2,6,8,10-tetraenoic acid]iron (1.73 g), 1-ethyl-3-(3-dimethylaminopropyl)carbodiimide hydrochloride (1.20 g), and HO-Bt (hydroxybenzotriazole) (1.02 g) were dissolved in dichloromethane (36.5 g), and the mixed solution was stirred for 5 minutes under an argon atmosphere. A solution of 2-hydroxy-2-methylpropylamine (1.02 g) dissolved in dichloromethane (18.3 mL) was added to the above solution at room temperature, and the resulting solution was stirred for 4.5 hours. At room temperature, a saturated sodium carbonate aqueous solution was added to the reaction solution and the water phase was extracted with ethyl acetate. The organic phase was washed with a saturated saline solution. After removing the organic phase under vacuum, the resulting residue was purified by silica gel chromatography (hexane/ethyl acetate=1/1→1/2→1/3) to obtain a yellow viscous oily product (1.73 g). The obtained oily product was recrystallized from an ether/hexane mixed solution to obtain a light yellow solid (1.43 g).

Data of the obtained compound are as follows:

$^1$H-NMR (CDCl$_3$, 400 MHz) δ: 1.25 (6H, s), 1.36 (1H, m), 1.43 (3H, d, J=5.9 Hz), 1.80 (1H, m), 1.87 (1H, dd J=8.8, 10.5 Hz), 2.21-2.36 (4H, m), 2.40 (1H, brs), 3.34 (2H, d, J=6.1 Hz), 5.04 (1H, dd, J=4.9, 8.0 Hz), 5.16 (1H, dd, J=4.9, 8.8 Hz), 5.31 (1H, td, J=6.6, 10.5 Hz), 5.42 (1H, t, J=10.5 Hz), 5.84 (1H, d, J=15.4 Hz), 5.86 (1H, brs), 6.87 (1H, td, J=6.3, 15.4 Hz); $^{13}$C-NMR (CDCl$_3$, 100 MHz), δ:19.15, 20.11, 26.58, 28.58, 31.48, 46.86, 56.13, 57.17, 82.23, 85.53, 124.28, 129.31, 131.62, 143.24, 165.87, 212.36;

ESI-MS m/z: +ESI 426 [M+Na]$^+$, 404 [M+H]$^+$, −ESI 402 [M−H]$^−$;

HRESI-MS m/z: 426.0977 (Calcd for C$_{19}$H$_{25}$NO$_5$FeNa: 426.0980);

IR (KBr): cm$^{-1}$: 3411, 3268, 2034, 1968, 1668, 1602, 1562, 622, 607, 566.

Experiment Example 7-2

Reaction was performed in the same manner as Experiment Example 7-1 except that the reagents used were changed to those shown in Table 4 below. Table 4 below shows yields of tricarbonyl[(8,9,10,11-η)-(2E,6Z,8E,10E)-N-(2-hydroxy-2-methyl-propyl)dodeca-2,6,8,10-tetraenamide]iron.

TABLE 4

| | Reaction conditions | Yield (%) |
|---|---|---|
| Experiment Example 7-1 | 2-hydroxy-2-methylpropylamine, 1-ethyl-3-(3-dimethylaminopropyl)carbodiimide hydrochloride, HO-Bt, CH$_2$Cl$_2$, r.t. | 95.3 |
| Experiment Example 7-2 | 2-chloro-1-methylpyridinium iodide, DIEA, 2-hydroxy-2-methylpropylamine, MeCN | 47.7 |

Experiment Example 8

Synthesis of (2E,6Z,8E,10E)-N-(2-hydroxy-2-methylpropyl)dodeca-2,6,8,10-tetraenamide (hydroxy-α-sanshool)

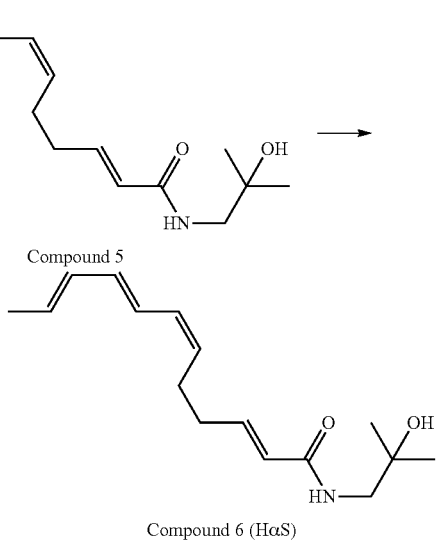

To a mixture product of tricarbonyl[(8,9,10,11-η)-(2E,6Z,8E,10E)-N-(2-hydroxy-2-methylpropyl)dodeca-2,6,8,10-tetraenamide]iron (50.0 mg) and trimethylamine N-oxide (102.1 mg) was added acetonitrile (2.0 mL) at room temperature under an argon atmosphere, and the resulting mixed solution was stirred for 2 hours. The precipitate was removed by filtration and water was added to the filtrate. The water phase was extracted with ethyl acetate. The organic phase was washed with a saturated saline solution and dried over with anhydrous sodium sulfate. The organic solvent was removed under vacuum and the mixture product was filtered through a cotton plug and evaporated to obtain a light yellow amorphous solid (30.5 mg). The yield was 93.4%.

Data of the obtained compound are as follows:

$^1$H-NMR (CDCl$_3$, 400 MHz) δ: 1.24 (6H, s), 1.78 (3H, d, J=6.7 Hz), 2.25-2.38 (4H, m), 3.33 (2H, d, J=6.1 Hz), 5.37 (1H, td, J=7.1, 10.9 Hz), 5.73 (1H, qd, J=7.1, 13.8 Hz), 5.84 (1H, td, J=1.6, 15.4 Hz), 5.85 (1H, brs), 6.02 (1H, t, J=10.9 Hz), 6.10 (1H, dd, J=10.4, 13.8 Hz), 6.18 (1H, dd, J=10.4, 13.8 Hz), 6.33 (1H, dd, J=10.9, 13.8 Hz), 6.86 (1H, td, J=6.5, 15.4 Hz).

Experiment Example 9

Stability tests of hydroxy-α-sanshool (HαS) and tricarbonyl[(8,9,10,11-η)-(2E,6Z,8E,10E)-N-(2-hydroxy-2-methylpropyl)dodeca-2,6,8,10-tetraenamide]iron (Compound 5)

(HPLC Analysis Conditions)
Column: TSK-GEL 80TS (φ4.6 mm×150 mm) (Tosoh, Japan); column temperature: 40° C.; flow rate: 1.0 mL/min; measurement wavelength: 200 to 400 nm; mobile phase: Liquid A acetonitrile, Liquid B 0.1% $Na_2S_2O_3$ aqueous solution (Liquid A: 40%, Liquid B: 60%); and measurement mode: isocratic mode.
(Measurement Method)
HαS (27.6 mg) and the compound 5 (50.4 mg) were diluted to 100 mL with anhydrous acetonitrile (HPLC grade) to prepare 0.26 mg/mL and 0.49 mg/mL sample solutions. The sample solutions, dispensed in 50 mL aliquots, were allowed to stand at room temperature for 24 hours under exposure to fluorescent light. Quantitative analysis was performed under the above HPLC analysis conditions to measure peak area values of the HαS and the diene iron complex compound (compound 5).
The value of the HαS reduced down to approximately 10% of an initial level after 24 hours from the irradiation of fluorescent light. On the other hand, the value of the diene iron complex compound (compound 5) stayed at a reduction to approximately 80% of the initial level. As obvious from the results, it has been found that the diene iron complex compound (compound 5) has higher solution stability against light than the HαS itself.

Experiment Example 10

Synthesis of 4-(1-phenyl-1H-tetrazole-5-ylsulfonyl)butanenitrile

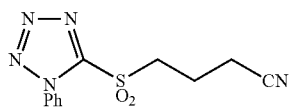

Compound 7

1) To a mixed solution of suspended potassium carbonate (15.6 g) and 1-phenyl-5-mercapto-1H-tetrazole (10 g) suspended in dimethylformamide (100 mL) was added 4-chlorobutyronitrile (1.2 mL) at room temperature, and the resulting solution was stirred at 80° C. for 2 hours. Water was added to the reaction solution and the water phase was extracted with ethyl acetate. The organic phase was washed with a saturated saline solution and dried over anhydrous sodium sulfate. The organic solvent was removed under vacuum to obtain sulfide.

2) To a mixed solution of the above sulfide and $Mo_{27}O_{24}(NH_4)_6 \cdot 4H_2O$ (2.08 g) suspended in ethanol (500 mL) was added dropwise 30% hydrogen peroxide solution (63 mL) at 0° C., and the mixed solution was stirred at 0° C. for 0.5 hours. Then, the mixed solution was stirred at room temperature for 19 hours. To the reaction solution was added a saturated sodium thiosulfate aqueous solution (0.6 mol/200 mL) and the reaction was stopped. The reaction solution was concentrated under vacuum. The water phase was extracted with ethyl acetate. The organic phase was washed with a saturated saline solution and dried over anhydrous sodium sulfate.

After moving the organic solvent under vacuum, the resulting residue was purified by silica gel column chromatography (hexane/ethyl acetate=1/1). The mixed solution was concentrated and recrystallized with hexane/methylene chloride to obtain 11.9 g of a white solid as a desired product (a yield of 76.5%).

Data of the obtained compound are as follows:
$^1$H-NMR (CDCl$_3$, 400 MHz) δ: 2.43 (2H, qui, J=7.1 Hz), 2.68 (2H, t, J=7.1 Hz), 3.92 (2H, t, J=7.1 Hz), 7.60-7.71 (5H, m). $^{13}$C-NMR (CDCl$_3$, 100 MHz), δ:16.13, 19.15, 54.28, 117.5, 124.93, 129.86, 131.68, 132.80, 153.12; ESI-LRMS: m/z: +ESI 300 [M+Na]$^+$, 278 [M+H]$^+$, −ESI 276 [M−H]$^-$.

Experiment Example 11-1

Synthesis of tricarbonyl[(6,7,8,9-η)-(4E,6E,8E)-deca-4,6,8-trienenitrile]iron

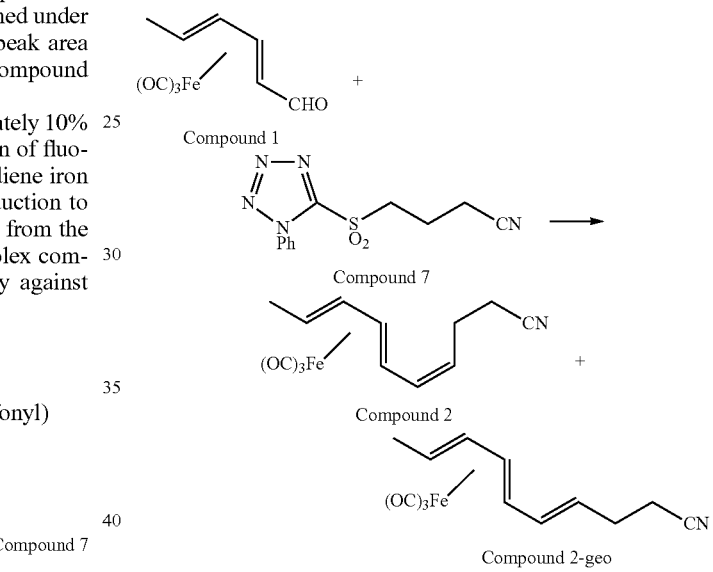

To a THF solution (100 mL) of the above compound 7 (3.63 g, 13 mmol) and the compound 1 (2.06 g, 8.72 mmol) was added dropwise a THF solution (0.2 mol/L, 100 mL) of KHMDS (potassium hexamethyldisilazide) at −78° C. under an argon atmosphere in 60 minutes. The mixed solution was stirred at −78° C. for 2 hours. After that, the reaction solution was stirred at room temperature for 22 hours and a saturated saline solution was added thereto. The water phase was extracted with ethyl acetate. The organic phase was washed with a saturated saline solution, dried over anhydrous sodium sulfate, filtered with a filter, and concentrated under vacuum. The resulting residue was purified by silica gel column chromatography (hexane/ethyl acetate=6/1) to obtain a yellow oily product. The product was purified by chromatography using an ODS column (50% acetonitrile) to obtain 1.52 g of a light yellow oily desired product.

Data of the obtained compound are as follows:
$^1$H-NMR (CDCl$_3$, 400 MHz) δ: 1.30-1.37 (1H, m), 1.42 (3H, d, J=6.1 Hz), 1.70 (1H, t, J=8.5 Hz), 2.28-2.40 (4H, m), 5.02 (1H, dd, J=4.9, 8.5 Hz), 5.15 (1H, dd, J=5.8, 9.4 Hz), 5.54 (1H, dd, J=9.4, 15.1 Hz), 5.62 (1H, dd J=5.8, 15.1 Hz); $^{13}$C-NMR (CDCl$_3$, 100 MHz), δ: 17.32, 19.19, 57.33, 59.67, 81.25, 85.37, 119.00, 126.14, 134.94; ESI-MS m/z: +ESI 310 [M+Na]$^+$, 288 [M+H]$^+$, −ESI 286 [M−H]$^-$; HRESI-MS m/z:

310.0145 (Calcd for $C_{13}H_{13}NO_3FeNa$: 310.0143); IR (film): $cm^{-1}$: 2036, 1964, 622, 610, 568.

Experiment Examples 11-2 to 11-18

Reaction was performed in the same manner as the above Experiment Example 11-1 except that the amount ratio (eq) of the compound 7 and the base, temperature, solvent, and reaction conditions to be used were changed to those shown in Table 5 below. Table 5 below shows yields of tricarbonyl[(6, 7,8,9-η)-(4E,6E,8E)-deca-4,6,8-trienenitrile]iron (compound 2-geo). The compound 2-geo represents a geometrical isomer of a compound 2. In addition, the isomer was able to be easily separated in the silica gel column and furthermore, the compound 2-geo was able to be obtained with high purity by recrystallization.

Additionally, a method employing a step of adding dropwise a solution of the compound 1 to a solution of a base-treated compound 7 is designated as method A, and as with the above Experiment Example 11-1, a method employing the step of adding dropwise a base to a solution of the compound 7 and the compound 1 is designated as method B.

−20° C. under an argon atmosphere, and the mixed solution was stirred at −20° C. for 1 hour. To the reaction solution was added 1 mol/L hydrochloric acid, and after stirring the resulting solution for 5 minutes, reaction was stopped. The water phase was extracted with ethyl acetate, and the organic phase was washed with a saturated saline solution and dried over anhydrous sodium sulfate. The organic solvent was removed under vacuum to obtain an aldehyde-geo.

2) To a mixed solution of $Zn(OTf)_2$ (11.0 g), TMEDA (2.43 mL), and DBU (8.1 mL) dissolved in THF (40 mL) was added diethylphosphonoacetate (2.62 mL) at room temperature under an argon atmosphere, and the resulting solution was stirred for 2 hours. Then, a THF solution (40 mL) of the above aldehyde-geo was added thereto, and the resulting mixed solution was stirred at room temperature for 18 hours.

To the reaction solution was added 1 mol/L hydrochloric acid, and after stirring the mixed solution for 5 minutes, reaction was stopped. The water phase was extracted with ethyl acetate. The organic phase was washed with a saturated saline solution and dried over anhydrous sodium sulfate. After removing the organic solvent under vacuum, the result-

TABLE 5

| Experiment Example | Method | Compound 7 (eq) | Base (eq) | Reaction conditions | Solvent | Yield | 2/2-geo |
|---|---|---|---|---|---|---|---|
| 11-2 | A | 1.1 | KHMDS (1.1) | −55° C.→−30° C. 1 h | DMF | 47 | 36/64 |
| 11-3 | A | 1.1 | KHMDS (1.1) | −78° C. 2 h→r.t. 23 h | THF | 46 | 2/98 |
| 11-4 | A | 1.5 | KHMDS (1.5) | −78° C. 1 h→r.t. 7 h | DME | 56 | 4/96 |
| 11-5 | A | 1.5 | KHMDS (2.0) | −78° C. 2 h→r.t. 16 h | THF | 41 | 4/96 |
| 11-6 | A | 1.5 | KHMDS (2.0) | −78° C. 1 h | DME | 41 | 7/93 |
| 11-7 | A | 1.7 | KHMDS (1.7) | −78° C. 1 h→0° C. 3 h | DME | 41 | 2/98 |
| 11-8 | A | 2.0 | KHMDS (2.0) | −60° C. 1 h→r.t. 3 h | DME | 41 | 2/98 |
| 11-9 | B | 1.0 | DBU (1.0) | −35° C. 1 h→r.t. 3 d | DME | 45 | 20/80 |
| 11-10 | B | 1.2 | NaHMDS (2.0) | −78° C. 1 h→r.t. 3 h | DME | 58 | 2/98 |
| 11-11 | B | 1.5 | t-BuOK (1.7) | −78° C. 1 h→r.t. 6 h | DME | 37 | 14/86 |
| 11-12 | B | 1.5 | KHMDS (1.5) 18-Crown-6-ether (1.5) | −78° C. 1 h→r.t. 21 h | DME | 46 | 16/84 |
| 11-13 | B | 1.2 | KHMDS (1.2) | −78° C. 1 h→r.t. 1 h | DME | 39 | 4/96 |
| 11-14 | B | 1.0 | KHMDS (2.0) | −78° C. 1 h, r.t. 22 h | DME | 48 | 6/94 |
| 11-15 | B | 2.0 | KHMDS (2.0) | −78° C. 1 h→10° C. 3 h | DME | 49 | 8/92 |
| 11-16 | B | 1.0 | KHMDS (2.0) | −78° C. 1 h, r.t. 20 h | THF | 62 | 5/95 |
| 11-17 | B | 1.5 | KHMDS (2.0) | −78° C. 2 h→r.t. 21 h | THF | 74 | 4/96 |
| 11-18 | B | 1.5 | KHMDS (2.0) | −78° C. 2 h→r.t. 21 h | THF | 6 | 3/97 |

Experiment Example 12-1

Synthesis of tricarbonyl[(8,9,10,11-η)-(2E,6E,8E,10E)-dodeca-2,6,8,10-tetraenoic acid]iron

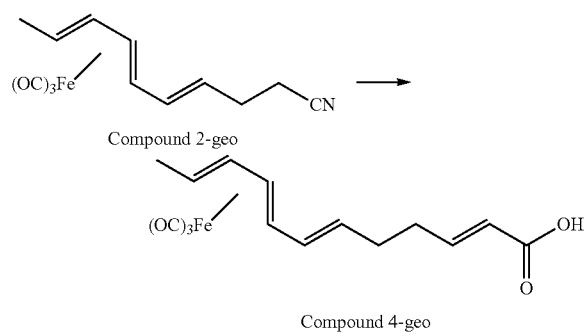

1) To a toluene solution (100 mL) of the above compound 2-geo (3.9 g) was added dropwise DIBAL-H (27.2 mL) at ing residue was purified by silica gel chromatography (hexane/ethyl acetate=4/1→1/1) to obtain a yellow viscous oily product. The product was recrystallized with hexane/methylene chloride to obtain 2.43 g (a yield of 53.7%) of a yellow solid desired product.

Data of the obtained compound are as follows:
mp 111.6-111.8° C. ($CH_2Cl_2$/hexane); $^1$H-NMR ($CDCl_3$, 400 MHz) δ: 1.30 (1H, m), 1.40 (3H, d, J=6.0 Hz), 1.75 (1H, t, J=9.6 Hz), 2.12-2.32 (4H, m), 5.00 (1H, dd, J=5.1, 8.7 Hz), 5.11 (1H, dd, J=5.1, 8.7 Hz), 5.43 (1H, dd, J=9.6, 15.1 Hz), 5.62 (1H, td, 6.8, 15.1 Hz), 5.83 (1H, d, J=14.9 Hz), 7.03 (1H, td, J=6.8, 14.9 Hz); $^{13}$C-NMR ($CDCl_3$, 100 MHz), δ: 19.18, 30.91, 31.83, 56.89, 61.20, 81.07, 84.94, 121.18, 129.64, 132.83, 151.04, 171.66, 212.43; ESI-MS m/z: +ESI 355 $[M+Na]^+$, 333 $[M+H]^+$, −ESI 331 $[M−H]^−$. HRESI-MS m/z: 355.0250 (Calcd for $C_{15}H_{16}NO_5FeNa$: 355.0245)., IR (KBr): $cm^{-1}$: 2924, 2038, 1953, 1689, 1644.

Experiment Examples 12-2 to 12-3

Reaction was performed in the same manner as the above Experiment Example 12-1 except that the stirring time (reaction time) and the amount of the compound 2-geo in the 2) were changed to those shown in Table 6 below. Table 6 below shows yields of tricarbonyl[(8,9,10,11-η)-(2E,6E,8E,10E)-dodeca-2,6,8,10-tetraenoic acid]iron (compound 4-geo).

TABLE 6

| | Amount of compound 2-geo | Reaction time in 2) (h) | Amount of compound 4-geo | Yield (%) | Presence or absence of recrystallization |
|---|---|---|---|---|---|
| Experiment Example 12-1 | 3.9 g | 18 | 2.43 g | 54 | Recrystallization |
| Experiment Example 12-2 | 216.4 mg | 18 | 124.2 mg | 50 | Not done |
| Experiment Example 12-3 | 227.6 mg | 4 | 185.6 mg | 70 | Not done |

Experiment Example 13

Synthesis of tricarbonyl[(8,9,10,11-η)-(2E,6E,8E,10E)-N-(2-hydroxy-2-methylpropyl) dodeca-2,6,8,10-tetraenamide]iron

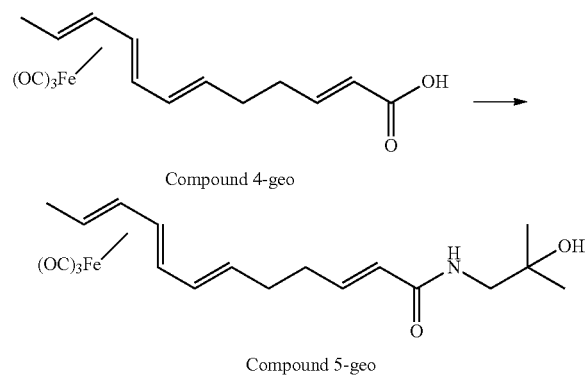

The compound 4-geo (101.3 mg), 1-ethyl-3-(3-dimethylaminopropyl)carbodiimide hydrochloride (71.0 mg), and HO-Bt (61.9 mg) were added to methylene chloride (2.1 mL), and the mixed solution was stirred at room temperature under an argon atmosphere for 5 minutes. To the mixed solution was added a methylene chloride solution (1.0 mL) of hydroxy-isobutylamine (59.8 g), and the resulting mixed solution was stirred for 4.5 hours. To the mixed solution was added a saturated sodium carbonate aqueous solution, and the water phase was extracted with ethyl acetate. The organic phase was washed with a saturated saline solution. After removing the organic solvent under vacuum, the resulting residue was purified by silica gel column chromatography (hexane/ethyl acetate=1/1→1/2) to obtain 118.0 mg (a yield of 97.5%) of a yellow viscous oily desired product.

Data of the obtained compound are as follows:
$^1$H-NMR (CDCl$_3$, 400 MHz) δ: 1.19-1.34 (1H, m), 1.24 (6H, m), 1.76 (1H, t, J=9.0 Hz), 2.13 (2H, dd, J=6.8, 13.8 Hz), 2.25 (2H, dd, J=6.8, 13.8 Hz), 3.33 (2H, d, J=6.1 Hz), 4.99 (1H, dd, J=4.9, 8.8 Hz), 5.11 (1H, dd, J=4.9, 8.8 Hz), 5.44 (1H, dd, J=9.8, 15.3 Hz), 5.64 (1H, td, J=6.8, 14.9 Hz), 5.81 (1H, d, J=15.3 Hz), 5.83 (1H, s), 6.82 (1H, td, J=6.8, 15.3 Hz); $^{13}$C-NMR (CDCl$_3$, 100 MHz), δ: 19.21, 27.35, 31.16, 31.62, 50.45, 56.98, 61.52, 71.10, 81.09, 84.94, 123.77, 130.28, 132.55, 144.20, 166.89; ESI-MS m/z: +ESI 426 [M+Na]$^+$, 404 [M+H]$^+$, −ESI 402 [M−H]$^−$. HRESI-MS m/z: 426.0972 (Calcd for C$_{19}$H$_{25}$NO$_5$FeNa: 426.0980). IR (film): cm$^{-1}$: 3302, 2918, 2035, 1961, 1669, 1627, 622, 610, 571.

Experiment Example 14

Synthesis of (2E,6E,8E,10E)-N-(2-hydroxy-2-methylpropyl)dodeca-2,6,8,10-tetraenenamide (hydroxy-β-sanshool)

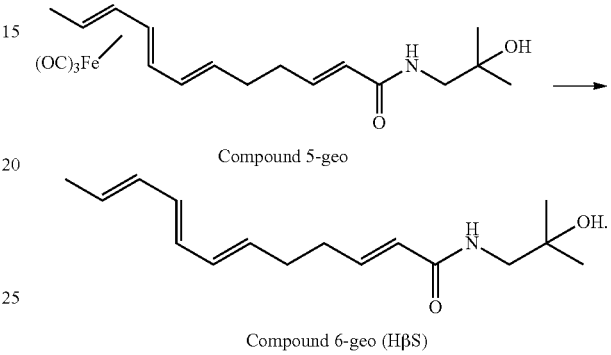

To a mixture product of the above compound 5-geo (98.8 mg) and trimethylamine-N-oxide (368 mg) was added acetonitrile (2.0 mL) at room temperature, and the mixed solution was stirred for 0.5 hours. The reaction solution was purified by silica gel column chromatography to obtain a light yellow product. The product was recrystallized with hexane/methylene chloride to obtain 53.4 mg of a white solid desired product.

Data of the obtained hydroxy-β-sanshool are as follows:
mp 84.0-85.0° C. (CH$_2$Cl$_2$/hexane); $^1$H-NMR (CDCl$_3$, 400 MHz) δ: 1.24 (6H, s), 1.76 (3H, d, J=7.1 Hz), 2.25-2.30 (4H, m), 3.33 (2H, d, J=6.1 Hz), 5.60-5.73 (2H, m), 5.82 (1H, d, J=15.4 Hz), 5.84 (1H, s), 6.02-6.14 (4H, m), 6.86 (1H, td, J=6.6, 15.4 Hz).

$^{13}$C-NMR (CDCl$_3$, 100 MHz), δ: 18.28, 27.37, 31.38, 31.90, 50.43, 71.12, 123.64, 129.39, 130.08, 131.47, 131.58, 131.67, 132.04, 144.49, 166.90.

The invention claimed is:
1. A diene iron complex compound characterized by being represented by the following general formula (I):

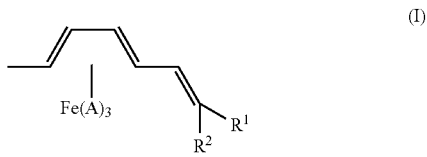

(wherein A represents CO, P(R$^A$)$_3$, CN, NO, SO(R$^A$)$_3$, or N(R$^A$)$_2$; R$^A$ represents a straight chain or branched chain alkyl group having 1 to 4 carbon atoms or an aryl group having 6 to 12 carbon atoms; and one of R$^1$ and R$^2$ represents a hydrogen atom and the other one thereof represents a structure represented by the following formula (II)):

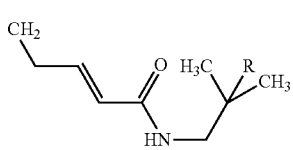

(II)

(wherein R represents a hydrogen atom, a hydroxyl group, or a methyl group).

2. A diene iron complex compound characterized by being represented by the following general formula (III):

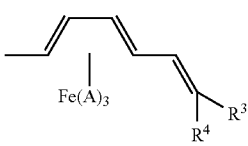

(III)

(wherein A represents CO, $P(R^A)_3$, CN, NO, $SO(R^A)_3$, or $N(R^A)_2$; $R^A$ represents a straight chain or branched chain alkyl group having 1 to 4 carbon atoms or an aryl group having 6 to 12 carbon atoms; and one of $R^3$ and $R^4$ represents a hydrogen atom and the other one thereof represents a 2-cyanoethyl group).

3. A method for producing a sanshool, characterized by comprising a step of reacting a diene iron complex compound represented by the following general formula (I):

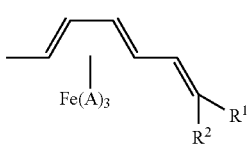

(I)

(wherein A represents CO, $P(R^A)_3$, CN, NO, $SO(R^A)_3$, or $N(R^A)_2$; $R^A$ represents a straight chain or branched chain alkyl group having 1 to 4 carbon atoms or an aryl group having 6 to 12 carbon atoms; and one of $R^1$ and $R^2$ represents a hydrogen atom and the other one thereof represents a structure represented by the following formula (II)):

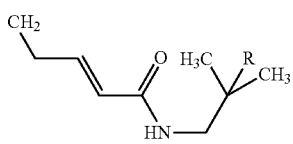

(II)

(wherein R represents a hydrogen atom, a hydroxyl group, or a methyl group) with a deprotecting agent.

4. The method for producing a sanshool according to claim 3, wherein the deprotecting agent is one selected from the group consisting of cerium (IV) compounds, trimethylamine N-oxide, pyridine N-oxide, iron (III) chloride, copper (II) chloride, dichlorodicyano benzoquinone, and hydrogen peroxide.

5. The method for producing a sanshool according to claim 3, further comprising:
a step of reducing a diene iron complex compound represented by the following general formula (III)

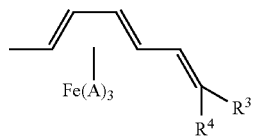

(III)

(wherein A represents CO, $P(R^A)_3$, CN, NO, $SO(R^A)_3$, or $N(R^A)_2$; $R^A$ represents a straight chain or branched chain alkyl group having 1 to 4 carbon atoms or an aryl group having 6 to 12 carbon atoms; and one of $R^3$ and $R^4$ represents a hydrogen atom and the other one thereof represents a 2-cyanoethyl group) to an aldehyde compound; and
a step of reacting the obtained aldehyde compound with dimethyl(isobutylcarbamoyl)methylphosphonate or diethyl(isobutylcarbamoyl)methylphosphonate to obtain the diene iron complex compound represented by the general formula (I).

6. The method for producing a sanshool according to claim 3, further comprising:
a step of reducing a diene iron complex compound represented by the following general formula (III)

(III)

(wherein A represents CO, $P(R^A)_3$, CN, NO, $SO(R^A)_3$, or $N(R^A)_2$; $R^A$ represents a straight chain or branched chain alkyl group having 1 to 4 carbon atoms or an aryl group having 6 to 12 carbon atoms; and one of $R^3$ and $R^4$ represents a hydrogen atom and the other one thereof represents a 2-cyanoethyl group) to an aldehyde compound;
a step of reacting the obtained aldehyde compound with diethylphosphonoacetic acid to obtain a diene iron complex compound represented by the following general formula (VII):

(VII)

(wherein A represents CO, $P(R^A)_3$, CN, NO, $SO(R^A)_3$, or $N(R^A)_2$; $R^A$ represents a straight chain or branched chain alkyl group having 1 to 4 carbon atoms or an aryl group having 6 to 12 carbon atoms; and one of $R^9$ and $R^{10}$ represents a hydrogen atom and the other one thereof represents a structure represented by the following formula (VIII)):

(VIII)

—COOH; and a step of reacting the obtained diene iron complex compound represented by the general formula (VII) with an amine represented by the following general formula (IX):

(IX)

(wherein R represents a hydrogen atom, a hydroxyl group, or a methyl group) to obtain the diene iron complex compound represented by the general formula (I).

7. The method for producing a sanshool according to claim 3, further comprising:
a step of reacting a compound represented by the following formula (X):

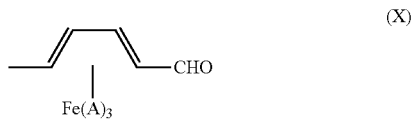

(X)

with 4-(1-phenyl-1H-tetrazole-5-ylsulfonyl)butanenitrile to obtain a diene iron complex compound represented by the following general formula (III):

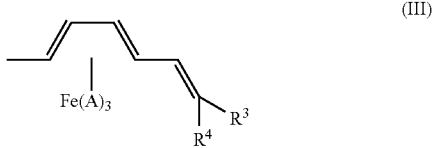

(III)

(wherein A represents CO, $P(R^A)_3$, CN, NO, $SO(R^A)_3$, or $N(R^A)_2$; $R^A$ represents a straight chain or branched chain alkyl group having 1 to 4 carbon atoms or an aryl group having 6 to 12 carbon atoms; and one of $R^3$ and $R^4$ represents a hydrogen atom and the other one thereof represents a 2-cyanoethyl group);

a step of reducing the diene iron complex compound represented by the general formula (III) to an aldehyde compound;
a step of reacting the obtained aldehyde compound with diethylphosphonoacetic acid to obtain a diene iron complex compound represented by the following general formula (VII):

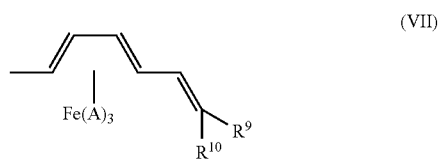

(VII)

(wherein A represents CO, $P(R^A)_3$, CN, NO, $SO(R^A)_3$, or $N(R^A)_2$; $R^A$ represents a straight chain or branched chain alkyl group having 1 to 4 carbon atoms or an aryl group having 6 to 12 carbon atoms; and one of $R^9$ and $R^{10}$ represents a hydrogen atom and the other one thereof represents a structure represented by the following formula (VIII)):

(VIII)

a step of reacting the obtained diene iron complex compound represented by the general formula (VII) with an amine represented by the following general formula (IX):

(IX)

(wherein R represents a hydrogen atom, a hydroxyl group, or a methyl group) to obtain the diene iron complex compound represented by the general formula (I).

* * * * *